United States Patent [19]
Kido et al.

[11] Patent Number: 5,792,567
[45] Date of Patent: Aug. 11, 1998

[54] TRIAZOLE DERIVATIVES AND ORGANIC ELECTROLUMINESCENT DEVICES PRODUCED THEREFROM

[75] Inventors: Junji Kido, Yonezawa; Takashi Uemura, Osaka; Hiroya Kimura, Osaka; Nobuyuki Okuda, Osaka; Yoshinobu Ueba, Osaka; Yasuko Okuda, Osaka; Hajime Osaka, Osaka, all of Japan

[73] Assignee: Sumitomo Electric Industries, Ltd., Osaka, Japan

[21] Appl. No.: 545,798

[22] PCT Filed: Mar. 15, 1995

[86] PCT No.: PCT/JP95/00440

§ 371 Date: Feb. 7, 1995

§ 102(e) Date: Feb. 7, 1995

[87] PCT Pub. No.: WO95/25097

PCT Pub. Date: Sep. 21, 1995

[30] Foreign Application Priority Data

Mar. 16, 1994 [JP] Japan .................. 6-045604

[51] Int. Cl.$^6$ ................................................. H05B 33/14
[52] U.S. Cl. .................... 428/690; 428/917; 313/504; 548/125
[58] Field of Search ................... 428/690, 691, 428/917; 313/504; 548/125

[56] References Cited

FOREIGN PATENT DOCUMENTS 0553950  8/1993  European Pat. Off. .
1393750  5/1975  United Kingdom .

OTHER PUBLICATIONS

Journal of Physical Chemistry Jun. 10, 1993, vol. 97, No. 23, pp. 6240–6248, Natio et al.

(List continued on next page.)

*Primary Examiner*—Charles Nold
*Attorney, Agent, or Firm*—Beveridge, Degrandi, Weilacher & Young, L.L.P.

[57] ABSTRACT

The triazole derivatives of this invention are expressed by the general formula (1).

The organic electroluminescent device of this invention have a layer containing at least one triazole derivative of the general formulas (1) and (2).

Such triazole derivatives are excellent in electron-transport efficiency, hole-blocking properties and heat resistance, and such organic electroluminescent devices are excellent in luminous efficiency, luminance and stability.

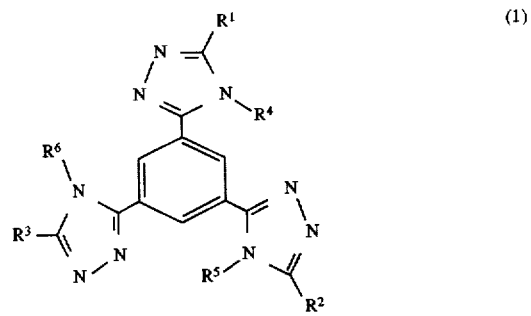

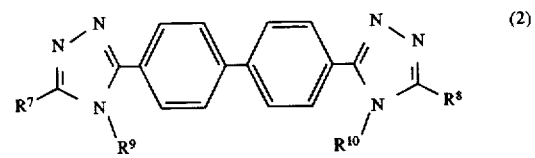

wherein $R^1$, $R^2$, $R^3$, $R^4$, $R^5$, $R^6$, $R^7$, $R^8$, $R^9$ and $R^{10}$ have the same meanings as indicated in the specification.

7 Claims, 4 Drawing Sheets

OTHER PUBLICATIONS

Applied Physics Letters, vol. 57, Aug. 6, 1990, pp. 531–533, Adachi et al.

Applied Physics Letters, vol. 63, No. 19, Nov. 8, 1993, Kido et al., pp. 2627–2629.

Optoelectronics Devices and Technologies, Jun. 1992, vol. 7, No. 1 Hamada et al. pp. 83–93.

Japanese J. Appl. Physical, vol. 32 (1993) pp. 917–920, Part 2, No. 7A, Jul. 1, 1993, Kido et al.

Department of Materials Science and Engineering, Yamagata University, Yonezawa, Ymagata 992, White Light–Emitting Organic El Devices Based on Poly(N–vinylcarbazole), pp. 1–8.

Chemical Abstracts, vol. 78, No. 18, May 7, 1973, pp. 126–127.

Chemical Abstracts, vol. 115, No. 24, Dec. 16, 1991, pp. 501–507.

Chemical Abstracts, vol. 122, No. 2 Jan. 9, 1995, pp. 67–74.

TRIAZOLE DERIVATIVES AND ORGANIC ELECTROLUMINESCENT DEVICES PRODUCED THEREFROM

TECHNICAL FIELD

The present invention relates to novel triazole derivatives and organic electroluminescent devices produced therefrom.

BACKGROUND ART

It has been considered that light emission of an organic electroluminescent device is caused by the phenomenon where holes and electrons injected from electrode are recombined within a luminescent layer to generate excitons, and the excitons excite molecules of luminescent materials constituting the luminescent layer. By employing fluorescent dye as a luminescent material, there can be obtained an emission spectrum as an electroluminescence, being equivalent to photoluminescence of the dye molecules.

Tang and Vanslyke recently proposed a device comprising two layers of a hole-transport layer and an electron-transport luminescent layer which efficiently emits green light at a lower voltage (about 10 V) compared with conventional organic electroluminescent devices having single-layer structure [C. W. Tang and S. A. Vanslyke; Appl. Phys. Lett., 51 (1987) 913]. The structure of the device is composed of an anode, a hole-transport layer, an electron-transport luminescent layer and a cathode, all of which are formed in this order on a glass substrate.

In this device, the hole-transport layer not only allows holes to be injected from the anode into the electron-transport luminescent layer, but prevents electrons injected from the cathode from escaping into the anode without recombining with the holes, so that the electrons are enclosed in the electron-transport luminescent layer. Thus, the electron confinement effect due to the hole-transport layer facilitates the recombination of the holes and the electrons compared with the conventional single-layer structure devices, resulting in substantial decrease in drive voltage.

Saito et al. showed that not only electron-transport layers but hole-transport layers can be the luminescent layer in the two-layer structure device [C. Adachi, T. Tsutsui and S. Saito; Appl. Phys. Lett., 55 (1989) 1489].

Saito et al. also proposed a three-layer structure organic electroluminescent device wherein an organic luminescent layer is interposed between a hole-transport layer and an electron-transport layer [C. Adachi, S. Tokito, T. Tsutsui and S. Saito; Jpn. J. Appl. Phys., 27 (1988) L269].

The two-layer structure device of Saito et al. is composed of an anode, a hole-transport luminescent layer, an electron-transport layer and a cathode, all of which are formed in this order on a glass substrate. In contrast to the previous device, the electron-transport layer not only allow electrons to be injected from the cathode into the hole-transport luminescent layer, but prevents the holes injected from the anode from escaping into the cathode while avoiding the recombination with the electrons, so that the holes are enclosed in the hole-transport luminescent layer. This hole confinement effect due to the electron-transport layer realizes substantial decrease in drive voltage, as in the previous device.

The three-layer structure device of Saito et al. was attained by a further improvement in the device of Tang et al. This device is composed of an anode, a hole-transport layer, a luminescent layer, an electron-transport layer and a cathode, all of which are formed in this order on a glass substrate. The hole-transport layer encloses electrons in the luminescent layer, and the electron-transport layer encloses holes in the luminescent layer, so that the recombination of the electrons and the holes within the luminescent layer is more efficient than the two-layer structure device.

Further, the electron-transport layer and the hole-transport layer prevent the excitons generated by the above recombination from escaping into either the anode or the cathode. Therefore, the three-layer structure device of Saito et al. may further increase the luminous efficiency.

Examples of hole-transport materials which constitute the above organic electroluminescent devices include aromatic tertiary amines such as triphenylamine. Examples of electron-transport material include oxadiazoles. Examples of luminescent material include tetraphenybutadiene derivatives, tris(8-quinolinolato)aluminum (III) complex, distyrylbenzene derivatives, distyrylbiphenyl derivatives and the like.

The inventors of this invention have confirmed that triazole compounds whose molecule has a triazole ring are excellent in electron-transport efficiency and that they are suitably used for electron-transport material.

The advantages of the above organic electroluminescent devices are:

(i) They can emit light of high luminance at a lower voltage than conventional electroluminescent devices comprising inorganic luminescent material;

(ii) They can easily increase the surface area because the respective layers can be formed not only by vacuum deposition but solution application; and (iii) They can emit light of multi-color depending upon the molecular design for organic molecule.

These devices, however, have the disadvantage that the luminance falls significantly during the use. It is therefore the urgent problems to improve the stability and to extend the light emitting lifetime.

One of the causes for this is presumed that since all of hole-transport material, electron-transport material and light emitting material used in the conventional organic electroluminescent devices have a relatively lower molecular weight, the glass transition temperature and crystallization temperature of these materials are lower so that they are poor in thermal properties.

Specifically, the use of such a lower molecular weight material whose thermal properties is poor may facilitate the deterioration of the material itself and the formation of exciplex between a light emitting material and a carrier-transport material, both of which are caused by Joule's heat generated when a current flows to a device. As a result, the luminous efficiency of the device decreases.

In organic electroluminescent devices, the interface between two organic layers and that between an organic layer and an electrode layer are required to be finished as smooth as possible in order to increase the carrier injection efficiency. For this reason, the organic layer is in amorphous state, though, the lower molecular weight material has a lower crystallization temperature, which would facilitate the development of the molecular cohesion due to the Joule's heat or prolonged standing in the atmosphere. As a result, the smoothness of the interfaces would be impaired by the crystallization, lowering the carrier-injection efficiency. This would lead to the drop in the luminous efficiency of the devices, shortening the light emitting lifetime.

This invention provides novel compounds that can form organic electroluminescent devices being excellent in luminous efficiency, luminance and stability, and also provides organic electroluminescent devices using the novel compounds being also excellent in these characteristics.

DISCLOSURE OF THE INVENTION

The compounds of this invention are triazole derivatives of the general formula:

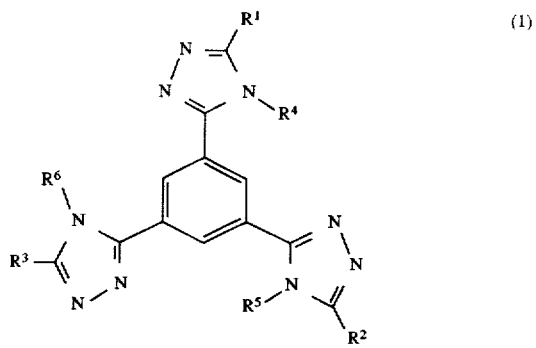

(1)

wherein $R^1$, $R^2$, $R^3$, $R^4$, $R^5$ and $R^6$ may be the same or different, each is hydrogen atom, halogen atom, alkyl, alkoxy, or alyl which may bear a substituent.

The organic electroluminescent devices of this invention have a layer comprising at least one triazole derivative selected from the triazole derivatives of the general formula (1) (hereinafter referred to as "oligomerized triazole derivative (1)") and the triazole derivatives of the general formula:

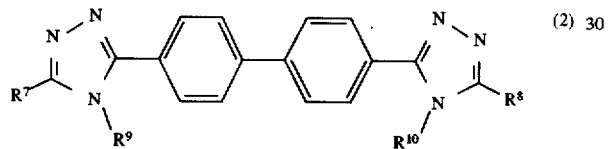

(2)

wherein $R^7$, $R^8$, $R^9$ and $R^{10}$ may be the same or different, each is hydrogen atom, halogen atom, alkyl, alkoxy, or alyl which may bear a substituent (hereinafter referred to as "oligomerized triazole derivative (2)").

Such a layer is preferred to be the electron-transport layer containing the oligomerized triazole derivatives as an electron-transport material.

In the oligomerized triazole derivatives of the general formula (1), each molecule has three triazole rings having electron-transport property and hole-blocking property. Further, the above triazole rings constitute the π-electron conjugated system that functions as electron-transport in association with the central benzene ring.

In the oligomerized triazole derivatives of the general formula (2), each molecule bears two triazole rings as described, and both triazole rings constitute a π-electron conjugated system in association with the central biphenyl ring.

Both types of oligomerized triazole derivatives are excellent in electron-transport efficiency and hole-blocking properties because they bear more triazole rings and more extended π-electron conjugated system than the conventional triazole compounds having lower molecular weight whose molecule has only one triazole ring.

In addition, each of the above triazole derivatives has a larger molecular weight than normal derivatives whose lower molecular weight is low, so that they exhibit higher values in melting point, glass transferring temperature and crystallization temperature, being excellent in thermal properties and heat resistance.

The organic electroluminescent devices having a layer which contains an oligomerized triazole derivative of the formula (1) or (2), being excellent in electron-transport efficiency, hole-blocking properties and heat resistance, not only increase the heat resistance of the layer but also significantly decrease the resistivity of the layer than the conventional triazole compounds having lower molecular weight. It is therefore possible to decrease the amount of the Joule's heat generated in the layer. This enables to retard the deterioration of the material itself and to inhibit the exciplex formed along with the light emitting material, both of which are caused by the Joule's heat.

Consequently, the amorphous and smooth interface can be retained by inhibiting the molecular cohesion due to the Joule's heat or prolonged standing in the atmosphere, thereby raising the luminous efficiency of the device to extend its light emitting lifetime.

Since both types of the oligomerized triazole derivatives possess outstanding characteristics for electron-transport material as previously described, the organic electroluminescent devices in which a layer containing the above derivative(s) is used as an electron-transport layer can further improve characteristics such as luminous efficiency, luminance and stability.

Additionally, since all of the above derivatives are excellent in hole-blocking properties as previously described, the combination of a layer containing such a derivative and a light emitting layer for blue or white light emission (neither of which has been obtained at high luminance) can raise the luminance of the light emitting layer to a required level for practical applications owing to the effect that the electron-transport layer encloses holes in the light emitting layer.

Meanwhile, both types of the oligomerized triazole derivatives are also usable for light emitting material and hole-transport material by changing the values of $R^1$, $R^2$, $R^3$, $R^4$, $R^5$ and $R^6$ in the general formula (1); and the values of $R^7$, $R^8$, $R^9$ and $R^{10}$ in the general formula (2). Accordingly, the use of the layer containing the above derivative(s) is not restricted to electron-transport layers.

The oligomerized triazole derivatives of the general formula (1) are novel materials that the present inventors has discovered. Although those of the general formula (2) are not novel, their applications to organic electroluminescent devices have never been studied. The present inventors were the first to produce the organic electroluminescent devices being excellent in the aforesaid properties by employing the latter derivatives.

PREFERRED EMBODIMENTS OF THE INVENTION

Figure 1A:
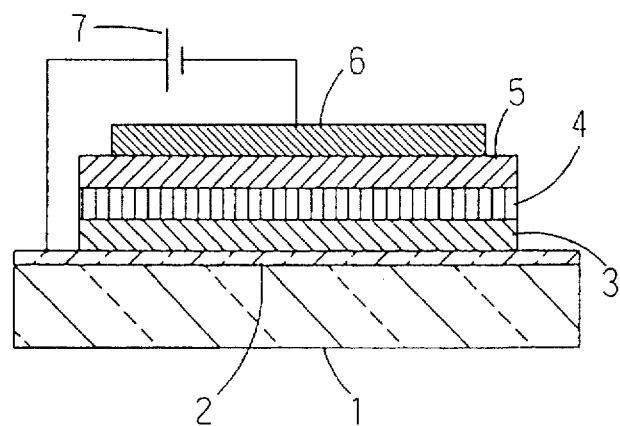
FIG. 1(a) is a sectional view illustrating the layer construction of the organic electroluminescent device prepared in Example I of this invention.

The oligomerized triazole derivatives of the general formula (1) will be described below.

A suitable value for $R^1$, $R^2$, $R^3$, $R^4$, $R^5$ or $R^6$ when it is alkyl is, for example, alkyl having 1 to 4 carbon atoms such as methyl, ethyl, normal propyl, isopropyl, normal butyl, isobutyl, the secondary butyl and the tertiary butyl.

A suitable value for $R^1$, $R^2$, $R^3$, $R^4$, $R^5$ or $R^6$ when it is alkoxy is, for example, alkoxy having 1 to 4 carbon atoms such as methoxy, ethoxy, normal propoxy, isopropoxy, normal butoxy, isobutoxy and the tertiary butoxy.

A suitable value for $R^1$, $R^2$, $R^3$, $R^4$, $R^5$ or $R^6$ when it is aryl is, for example, phenyl, tolyl, xylyl, biphenyl, naphthyl, anthryl and phenanthryl.

Examples of the substituents which may be substituted by aryl include, for example, halogen atom, cyano, and aryl amino, the above alkyl groups, the above alkoxy groups and the above aryl groups.

$R^1$, $R^2$, $R^3$, $R^4$, $R^5$ and $R^6$ may differ from one another. But in view of facility in synthesis, it is desirable that $R^1$, $R^2$ and $R^3$ are all $R^a$, and $R^4$, $R^5$ and $R^6$ are all $R^b$, as shown in the general formula:

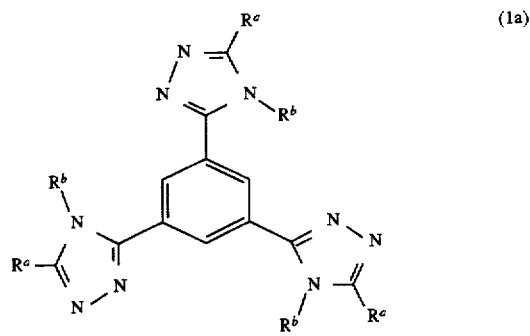

The oligomerized triazole derivatives of the general formula (1a) can be synthesized by the reaction scheme:

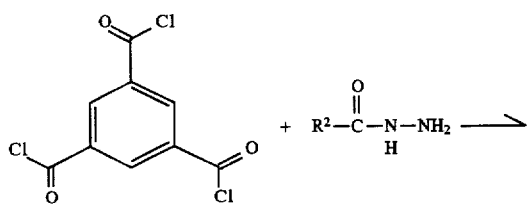

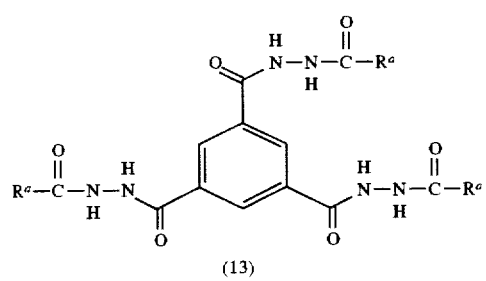

A 1,3,5-benzenetricarbonyl trichloride of the formula (11) and a carboxylic acid hydrazide compound of the general formula (12), including $R^a$, are allowed to react with a suitable solvent (e.g., dehydrated pyridine) to give a tris-(dihydrazide) compound of the general formula (13).

The above carboxylic acid hydrazide compound is prepared by reacting a carbonyl chloride including $R^a$ and a hydrazine in a suitable solvent (e.g., ethanol).

Then, the above tris-(dihydrazide) compound of the formula (13) and a primary amine including $R^b$ are subjected to ring closure reaction using phosphorus trichloride ($PCl_3$) in a suitable solvent (e.g., ortho-dichlorobenzene) to give an oligomerized triazole derivative of the general formula (1a).

As exemplified compounds of the oligomerized triazole derivatives of the general formula (1), there can mention, for example, without being limited thereto, the following compound of the formula:

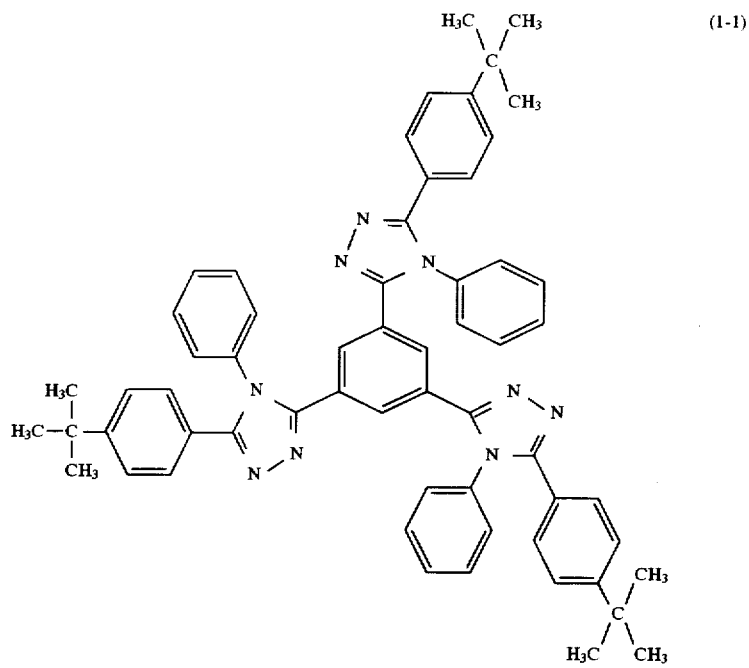

(1-1)

Other oligomerized triazole derivatives of the general formula (2) will be described hereinafter.

A suitable value for $R^7$, $R^8$, $R^9$ or $R^{10}$ when it is alkyl, alkoxy, aryl, or a substituent which may be substituted by aryl is, for example, the same groups as mentioned above.

$R^7$, $R^8$, $R^9$ and $R^{10}$ may differ from one another. But in view of facility in synthesis, it is desirable that $R^7$ and $R^8$ are both $R^c$; and $R^9$ and $R^{10}$ are both $R^d$, as shown in the general formula:

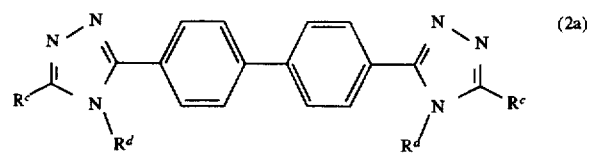

(2a)

The oligomerized triazole derivatives of the general formula (2a) can be synthesized by processes of the following reaction scheme:

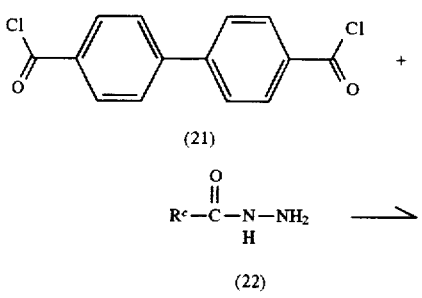

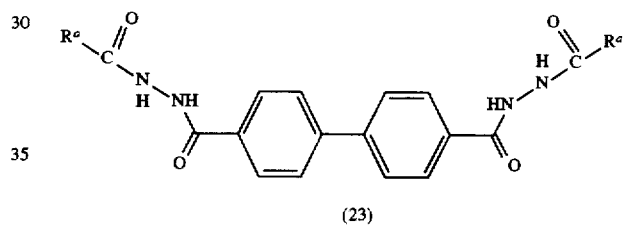

(23)

A 4,4'-biphenylcarbonyl dichloride of the formula (21) and a carboxylic acid hydrazide compound of the general formula (22), including $R^c$, are allowed to react with a suitable solvent (e.g., dehydrated pyridine) to give a bis-(dihydrazide) compound of the general formula (23).

The above carboxylic acid hydrazide compound can be prepared by reacting a carbonyl chloride including $R^c$ and a hydrazine in a suitable solvent (e.g., ethanol).

Then, the above bis-(dihydrazide) compound of the formula (23) and a primary amine including $R^d$ are subjected to ring closure reaction using phosphorous trichloride ($PCl_3$) in a suitable solvent (e.g., ortho-dichlorobenzene) to give an oligomerized triazole derivative of the general formula (2a).

Exemplified compounds of the oligomerized triazole derivatives of the general formula (2) include, without being limited thereto, for example, the respective compounds disclosed in British Patent Specification No. 1393750 and the compounds of the formulas (2-1) to (2-9):

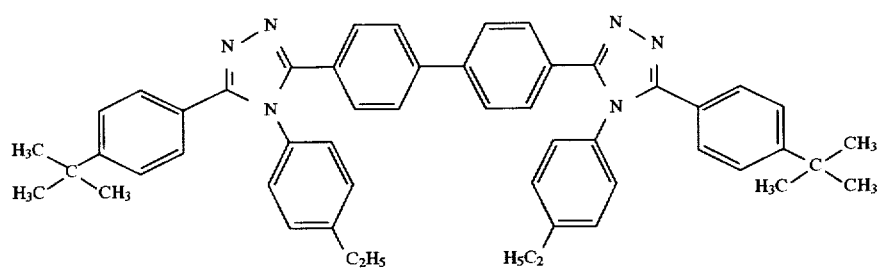 (2-1)
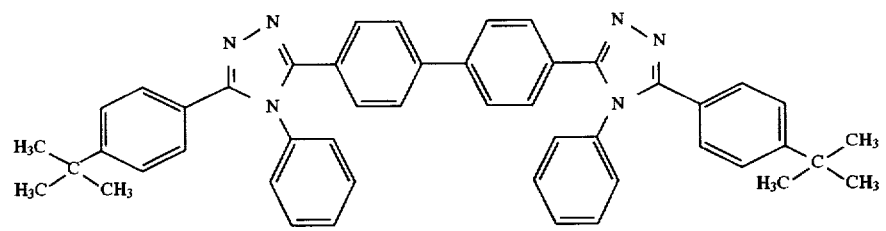 (2-2)
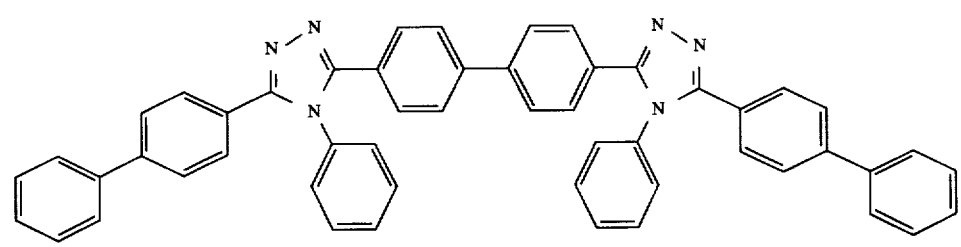 (2-3)
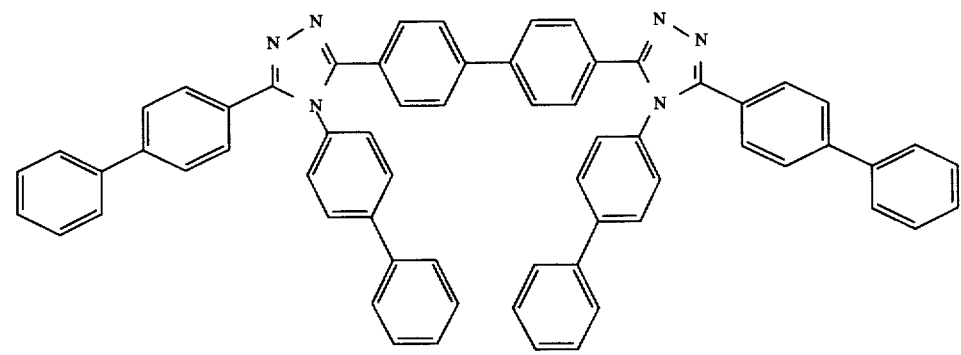 (2-4)
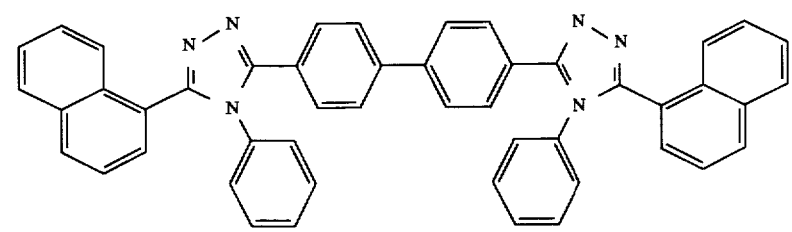 (2-5)
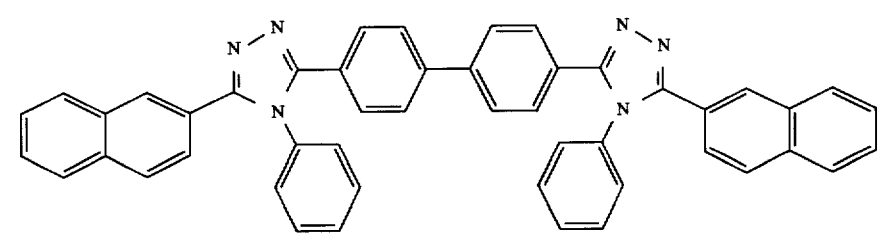 (2-6)

-continued

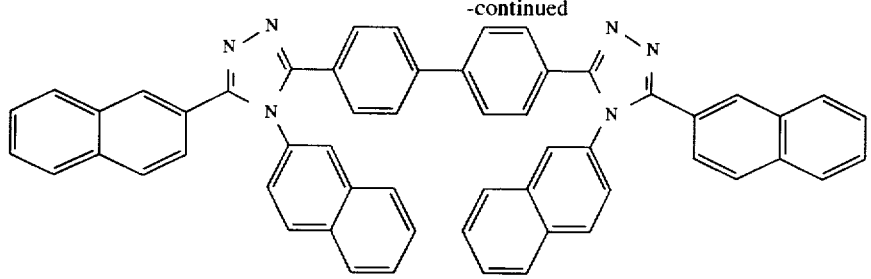
(2-7)

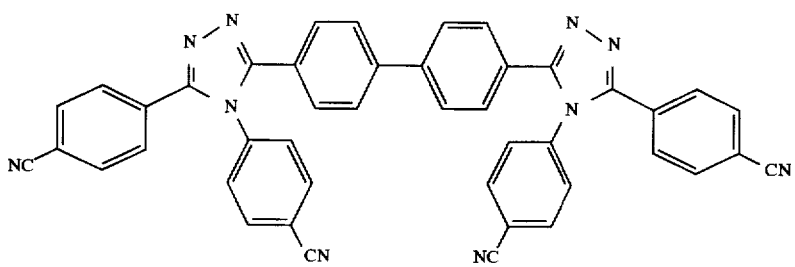
(2-8)

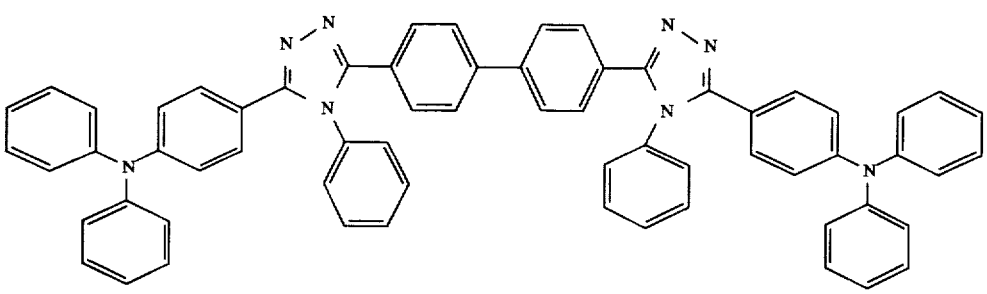
(2-9)

The organic electroluminescent devices of this invention will be described hereinafter.

In the organic electroluminescent devices of this invention, it is essential to have a layer containing at least one selected from the oligomerized triazole derivatives of the general formulas (1) and (2), but such a layer is preferred to be an electron-transport layer containing the oligomerized triazole derivative(s) as an electron-transport material.

Specifically, the above electron-transport layer is principally composed of one or more kinds of the oligomerized triazole derivatives containing either or both types of the oligomerized triazole derivatives of the general formulas (1) and (2), as electron-transport materials. Examples of such electron-transport layers include, for example, those made of the oligomerized triazole derivative(s) alone and those prepared by molecularly dispersing one or more kinds of the oligomerized triazole derivatives into a suitable resin binder.

The former electron-transport layer can be formed by depositing the oligomerized triazole derivative(s) on a substrate by vapor deposition such as vacuum deposition, or by solution application (i.e., to apply, on a substrate, a solution wherein the oligomerized triazole derivative(s) is dissolved in a suitable solvent, followed by drying). The latter can be formed by another solution application (i.e., to apply, on a substrate, a solution wherein the materials for the electron-transport layer are dissolved in a suitable solvent, followed by drying).

Both types of the electron-transport layers may contain other materials such as various additives which do not inhibit the function of the oligomerized triazole derivatives.

The film thickness of the electron-transport layer is not specifically limited in this invention, but it should be set to the optimum range depending upon its structural characteristics, i.e., whether it belongs to the former or the latter type.

Since any other structural restrictions are not imposed to the above organic electroluminescent devices, it is possible to apply them to any structures, e.g., the conventional two-layer, and multi-layers comprising three or more layers.

In the devices having the multi-layer structure, materials for other layers than the electron-transport layer are not particularly limited in this invention. There can be selected from a variety of the conventional materials for the respective layers. Also, the film thickness of the respective layers is not specifically limited in this invention. The individual layers can be formed by the aforesaid solution application or vapor deposition such as vacuum deposition, as in the electron-transport layers. Each layer may contain other materials such as resin binders and various additives which do not relate directly to each layer's function.

As previously described, the oligomerized triazole derivatives of the general formulas (1) and (2) are also usable for light emitting material and hole-transport material by changing the values of $R^1$, $R^2$, $R^3$, $R^4$, $R^5$ and $R^6$; and $R^7$, $R^8$, $R^9$ and $R^{10}$, it is therefore possible to produce the organic electroluminescent devices having the structure where the oligomerized triazole derivative(s) is used for other layers than the electron-transport layer, i.e., the light emitting layer and the hole-transport layer.

FIELD OF INDUSTRIAL APPLICABILITY

As described in the foregoing, both the oligomerized triazole derivatives of the general formula (1) and those of the general formula (2) have superior electron-transport efficiency, hole-blocking properties and heat resistance.

Hence the organic electroluminescent devices having the layer containing the oligomerized triazole derivative(s) of the general formula (1) or/and (2), are excellent in luminous efficiency, luminance and stability. Because they can emit light at high luminance and depress heat generation when the device emits light and they also depress the deterioration and the crystallization of the above triazole derivatives due to the heat generation.

The organic electroluminescent devices having an electron-transport layer, which contains the oligomerized triazole derivative(s) as an electron-transport material, are excellent in luminous efficiency, luminance and stability because the above oligomerized triazole derivatives are excellent in electron-transport efficiency.

Therefore, the organic electroluminescent devices of this invention can be driven at a lower voltage, and are useful for producing large-area luminescent devices having flexibility derived from the organic material. Thus, they have a bright prospect of the applications in the fields of indications, illuminations, displays and the like.

EXAMPLES

The invention will be better understood by the following Examples and Comparative Example which show by way of example.

I. Preparation of Oligomerized Triazole Derivative

A solution of 1,3,5-benzenetricarbonyl trichloride of the formula (11) (6.5 g, 25 mmol) and a carboxylic acid hydrazide compound of the general formula (12) wherein $R^a$ is 4-tert-buthylphenyl (14.1 g, 75 mmol) in 300 ml of dehydrated pyridine as a solvent, was heated to 110° C. with stirring in a nitrogen atmosphere for 20 hours. After the reaction was completed, the solvent was distilled away from the reaction mixture, and the precipitate was washed with water to give a tris-(dihydrazide) compound of the general formula (13) wherein each $R^a$ is 4-tert-butylphenyl (16.1 g, 90% yield).

The tris-(dihydrazide) compound thus obtained (7.3 g, 0.01 mol) and an aniline as a primary amine which includes phenyl for $R^b$ (16.8 g, 0.18 mol) were dissolved in 100 ml of ortho-dichlorobenzene as a solvent, together with phosphorous trichloride (4.1 g, 0.03 mol), and the mixture was heated to 180° C. with stirring for 12 hours. After the reaction was completed, the solvent was distilled away from the reaction mixture, and the resulting precipitate was once washed with 0.5N hydrochloric acid and once with distilled water to give a crystal (2.7 g, 30% yield).

The elemental analysis for the crystal was conducted by CHN mass spectrometry to obtain the following results:

Calcd.(% by weight): C, 80.6; H, 5.3; N, 14.1

Found (% by weight): C, 80.2; H, 5.4; N, 13.9

It should be noted that the calculated values and the found values almost agreed.

The mass spectrum of the crystal was determined by GC-MASS, and there found to be of one-component having a single peak of a molecular weight of 894.

Thus the crystal was found to be identical with the oligomerized triazole derivative of the formula (1-1), whose molecular weight was 894.1.

It was tried to determine the melting point of the crystal by DSC, though, it was above the decomposition temperature. Based on this, it would be predicted that the melting point would go over 360° C., and that the glass transferring temperature would exceed 150° C.

The resistivity of the crystal was $10^8$ [Ω·cm].

II. Preparation of Oligomerized Triazole Derivative

A solution of 4,4'-biphenylcarbonyl dichloride of the formula (21) (5.58 g, 20 mmol) and a carboxylic acid hydrazide compound of the general formula (22) wherein $R^c$ is 4-tert-butylphenyl (7.69 g, 40 mmol) in 150 ml of dehydrated pyridine was heated to 100° C. with stirring in a nitrogen atmosphere for 20 hours. After the reaction was completed, the solvent was distilled away from the reaction mixture, and the precipitate was washed with water to give a bis-(dihydrazide) compound of the general formula (23) wherein $R^c$ was 4-tert-buthylphenyl (8.27 g, 70% yield).

The bis-(dihydrazide) compound thus obtained (5.91 g, 0.01 mol) and a p-ethylanyline being a primary amine which includes 4-ethylphenyl for $R^d$ (14.5 g, 0.12 mol) were dissolved in 100 ml of ortho-dichlorobenzene as a solvent, together with phosphorus trichloride ($PCl_3$) (2.7 g, 0.02 mol), and the mixture was heated to 180° C. with stirring for 12 hours. After the reaction was completed, the solvent was distilled away from the reaction mixture, and the resulting precipitate was once washed with 0.5N hydrochloric acid and once with distilled water to give a crystal (1.5 g, 20% yield).

The elemental analysis for the crystal was conducted by CHN mass spectrometry. Its results was as below:

Calcd.(% by weight): C, 82.1; H, 6.9; N, 11.0

Found (% by weight): C, 82.3; H, 6.8; N, 10.9

It should be noted that the calculated values and the found values almost agreed.

The mass spectrum of the crystal was determined by GC-MASS, and there found to be of one-component having a single peak whose molecular weight was 761.

Thus the crystal was found to be identical with the oligomerized triazole derivative of the formula (2-1), whose molecular weight was 761.03.

The melting point of the crystal was found to be 350° C. by DSC, and the glass transferring temperature was predicted to be 142° C.

The resistivity of the crystal was $10^8$ [Ω·cm].

Example 1

On an ITO (indium-tin-oxide) coated glass substrate having a sheet resistance of 15 Ω/□ (ITO film thickness: 1500 to 1600 Å, manufactured by Asahi Glass Co., Ltd.), (i) an N,N'-diphenyl-N,N'-bis(3-methylphenyl)-1,1'-biphenyl-4,4'-diamine (hereinafter referred to as "TPD") of the formula:

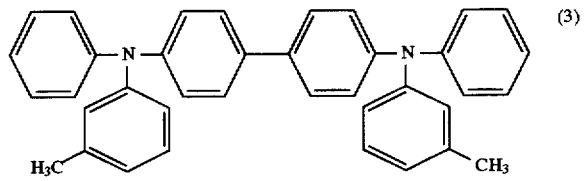

as a light emitting material having hole-transport properties, (ii) an oligomerized triazole derivative of the formula (1-1) as an electron-transport material, and (iii) a tris(8-quinolinolato)aluminum (III) complex (hereinafter referred to as "Alq") of the formula:

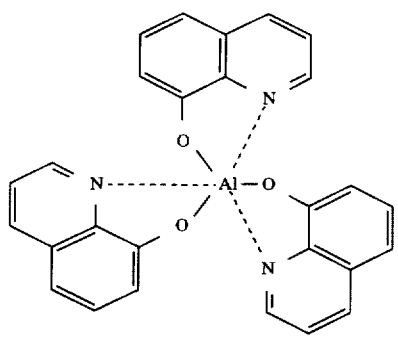

(4)

as a second electron-transport material were deposited in this order by vacuum deposition to form a lamination layer.

The luminescent region was expressed by a square being 0.5 cm in side. The deposition conditions for each layer was as follows:

Vacuum pressure: $2\times10^{-5}$ Torr;

Temperature of the substrate: Room temperature; and

Deposition rate: 2 to 4 Å/sec. Each film thickness was as follows:

TPD layer(the hole-transport luminescent layer): 500 Å;

The oligomerized triazole derivative layer (the first electron-transport layer): 200 Å; and Alq layer (the second electron-transport layer): 300 Å.

Then, on the Alq layer, magnesium was codeposited with silver to form an Mg/Ag electrode layer having a film thickness of 3000 Å[Mg/Ag=10/1 (molar ratio)], to prepare an organic electroluminescent device of three-layer structure. The deposition rate of the electrode layer was 10 Å/sec.

FIG. 1(a) shows the layer structure of the electroluminescent device thus obtained. In FIG. 1(a), the reference numeral 1 denotes a glass substrate, 2 denotes the ITO film, 3 denotes the TPD layer (the hole-transport luminescent layer), 4 denotes the oligomerized triazole derivative layer (the first electron-transport layer), 5 denotes the Alq layer (the second electron-transport layer), 6 denotes the Mg/Ag electrode layer and 7 denotes a power source for applying a bias voltage to the above device.

The ITO film 2 and the Mg/Ag electrode layer 6 thus prepared were used as an anode and a cathode, respectively, and the bias voltage from the power source 7 was applied between a couple of electrodes at room temperature in air to emit light. Its luminance was measured on a luminance meter (Model No. LS-100, manufactured by Minolta Co., Ltd.).

At a drive voltage of 16 V, there was observed a blue light emission having an luminance of 3700 cd/m² originated from the TPD layer 3. Even when the device was preserved at room temperature for several days, its appearance remained unchanged, and its luminance was virtually invariant.

Example 2

The procedure of Example 1 was repeated except that as a hole-transport luminescent layer, a dip coating film made of polyvinylcarbazole (hereinafter referred to as "PVK") having a repeating unit of the formula:

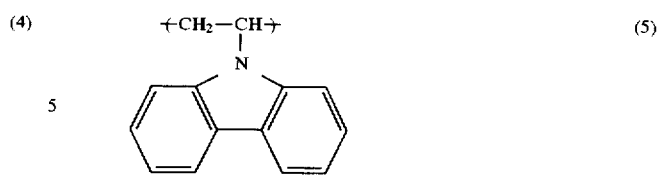

(5)

was used in place of the vacuum deposited TPD film to prepare an organic electroluminescent device.

The dip coating was conducted as follows:

Into a coating material wherein the PVK was dissolved in dichloroethane (8 g/liter), a similar ITO coated glass substrate as used in Example 1 was dipped and then drawn it out at a speed of 10 cm/min., followed by drying at 50° C. for 10 minutes. The film thickness of the PVK layer was 500 Å.

Figure 1B:
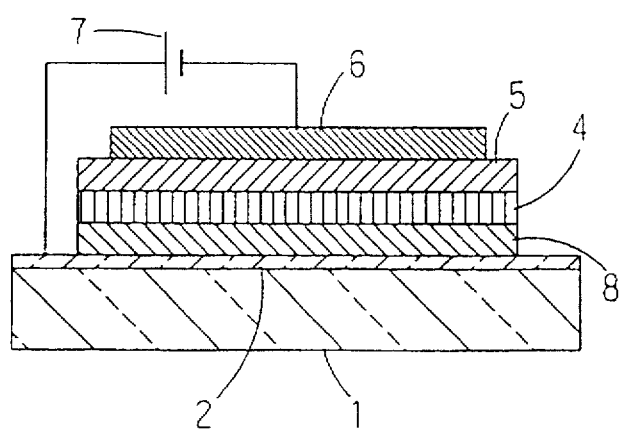
FIG. 1(b) is a sectional view illustrating the layer construction of the organic electroluminescent device prepared in Example 2 of this invention.

FIG. 1(b) shows the film structure of the organic electroluminescent device thus obtained. In FIG. 1(b), the reference numerals 1, 2 and 4–7 have the same meanings as in FIG. 1(a), and 8 denotes the PVK layer.

The luminance of this device was determined in the same manner as in Example 1. At a drive voltage of 14 V, (220 mA/cm²), there was observed a blue light emission having an luminance of 700 cd/m² originated from the PVK layer 8. Even when the device was preserved at room temperature for several days, its appearance remained unchanged, and its luminance was virtually invariant.

Example 3

A coating material was prepared by dissolving, in 30 ml of dichloromethane, (a) 150 mg of the TPD (b) 150 mg of polyethersulfone (hereinafter referred to as "PES") having a repeating unit of the formula:

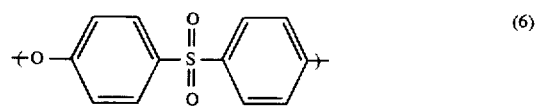

(6)

(c) 0.1 mg of tetraphenylbutadiene (hereinafter referred to as "TPB") as a fluorescent dye, whose fluorescent wavelength was 440 nm, expressed by the formula:

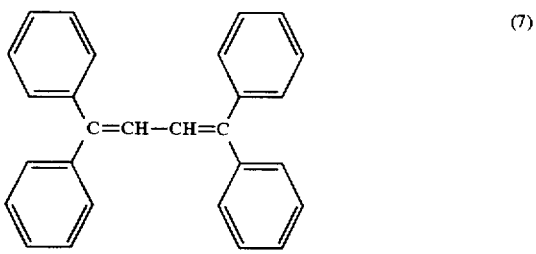

(7)

(d) 8.5 mg of coumarine 6 as a fluorescent dye, whose fluorescent wavelength was 480 nm, expressed by the formula:

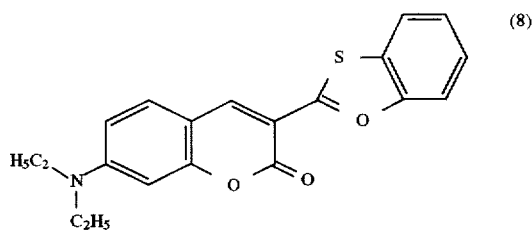

(8)

(e) 12 mg of 4-dicyanomethylene-2-methyl-6-p-dimethylaminostyryl-4H-pyran (hereinafter referred to as "DCM") as a fluorescent dye, whose fluorescent wavelength was 550 nm, expressed by the formula:

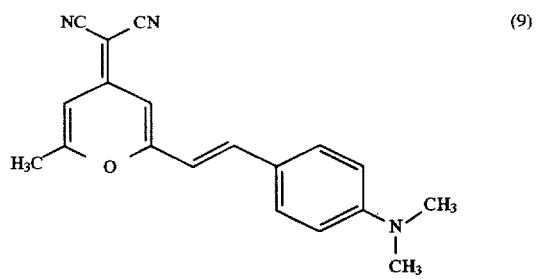

(9)

The coating material was applied on an ITO (indium-tin-oxide) coated glass substrate (ITO film thickness: 1500 to 1600 Å, manufactured by Asahi Glass Co., Ltd.) by dip coating whose drawing-out speed was 10 cm/min. There was obtained a hole-transport luminescent layer wherein fluorescent dye was being dispersed. Its film thickness was 500 Å.

Then, on the above light emitting layer, (i) the oligomerized triazole derivative of the formula (2-1) as a first electron-transport material, and (ii) the Alq as a second electron-transport material were deposited in this order by vacuum deposition to form a lamination layer.

The luminescent region was expressed by a square being 0.5 cm in side. The deposition conditions for each layer was as below:

Vacuum pressure: $2 \times 10^{-5}$ Torr;

Temperature of the substrate: Room temperature; and

Deposition rate: 2 to 4 Å/sec.

Each film thickness was:

The hole-transport luminescent layer: 500 Å;

The oligomerized triazole derivative layer (the first electron-transport layer): 200 Å; and The Alq layer (the second electron-transport layer): 300 Å.

Then, on the Alq layer, magnesium was codeposited with silver to form an Mg/Ag electrode layer having a film thickness of 3000 Å[Mg/Ag=10/1 (molar ratio)], to prepare an organic electroluminescent device of three-layer structure. The deposition rate of the electrode layer was 10 Å/sec.

Figure 2A:
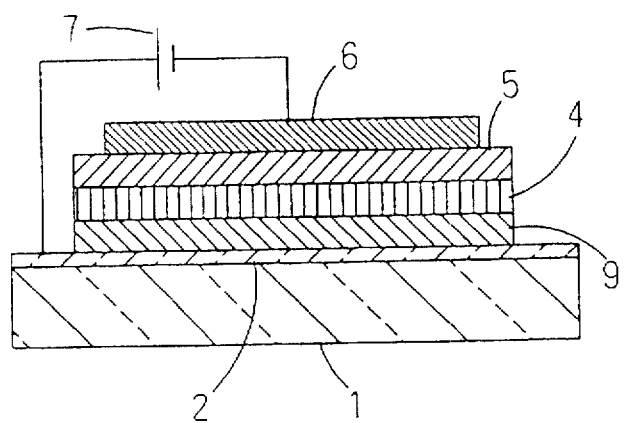
FIG. 2(a) is a sectional view illustrating the layer construction of the organic electroluminescent device prepared in Example 3 of this invention.

FIG. 2(a) shows the film structure of the organic electroluminescent device thus obtained. In FIG. 2(a), the reference numerals 1, 2 and 4–7 have the same meanings as in FIG. 1(a), and 9 denotes the above hole-transport luminescent layer.

Figure 3:
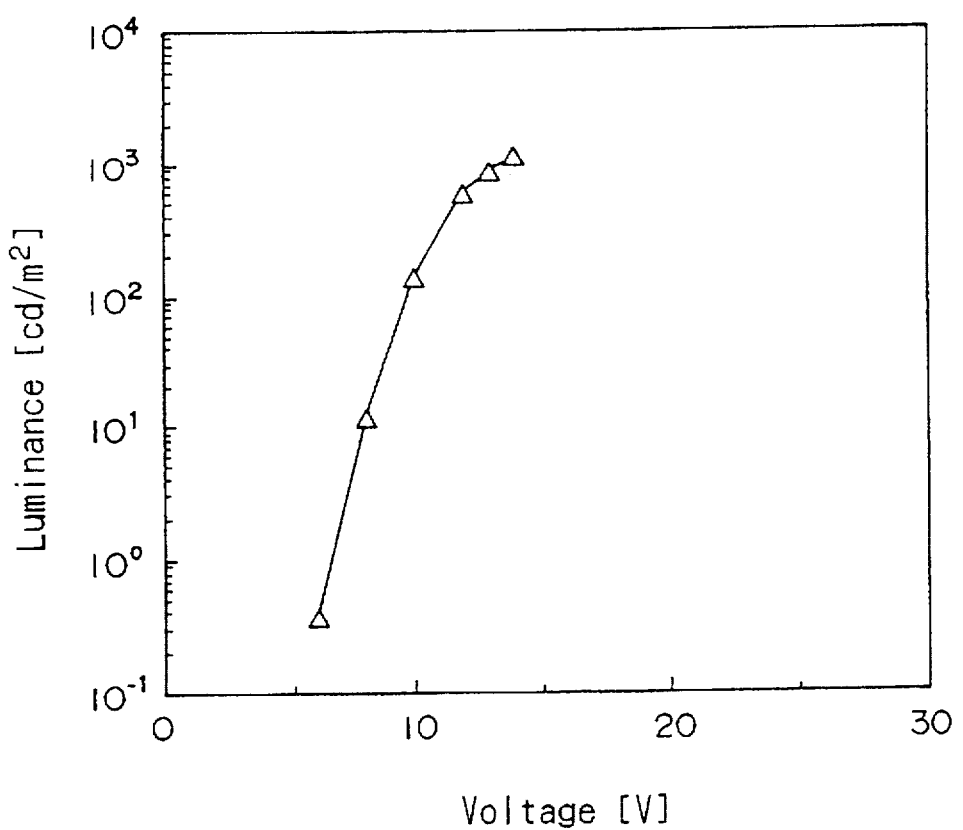
FIG. 3 is a graph illustrating the correlation between the drive voltage and the luminance in the organic electroluminescent device prepared in Example 3 of this invention.

The luminance of the above device was determined in the same manner as in Example 1. At a drive voltage of 10 V (10 mA/cm²), there was observed a white light emission originated from the hole-transport luminescent layer 9, exhibiting the correlation between the voltage and the luminous properties as shown in FIG. 3.

The CIE coordinate measurements for the above luminescent color showed that X=0.34; Y=0.33, thus being pure white. Even when the device was preserved at room temperature for several days, its appearance remained unchanged, and its luminance was virtually invariant.

Example 4

The procedure of Example 3 was repeated except that a solution of the TPD (150 mg) and the PES (150 mg) in 30 ml of dichlolomethane was used as a coating material for hole-transport luminescent layer, to prepare an organic electroluminescent device having three-layer structure.

Figure 4:
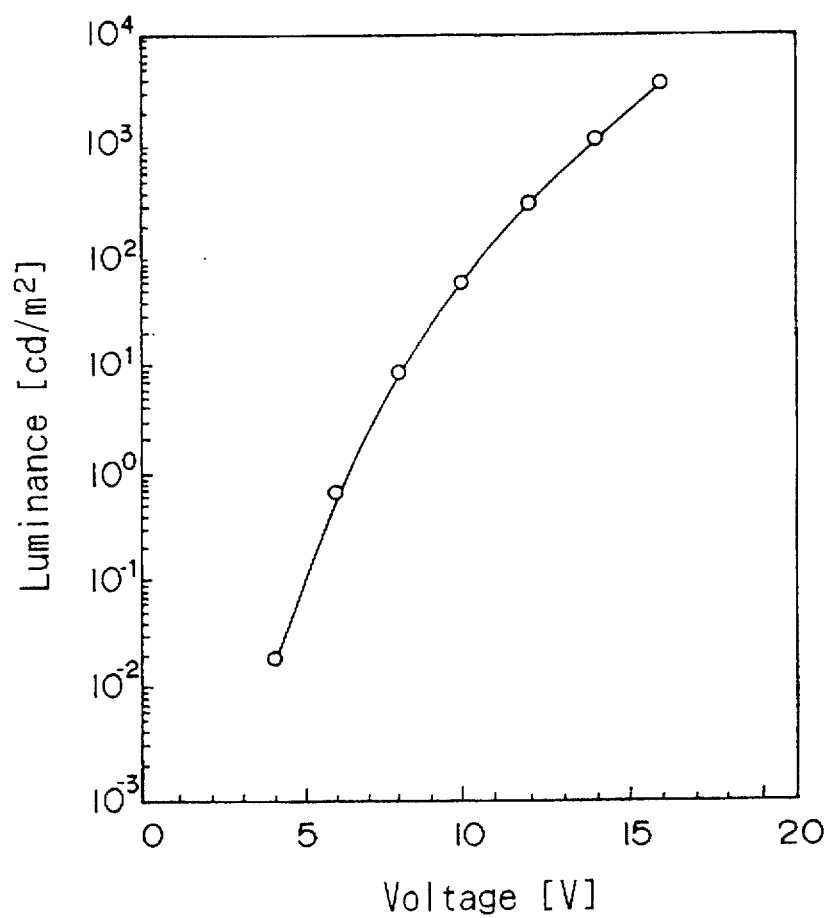
FIG. 4 is a graph illustrating the correlation between the voltage and the luminescent in the organic electroluminescent device prepared in Example 4 of this invention.

The luminance of this device was determined in the same manner as in Example 1. At a drive voltage of 10 V (40 mA/cm²), there observed a blue light emission originated from the light emitting layer, which exhibited the correlation between the voltage and the luminous properties as shown in FIG. 4. Even when the device was preserved at room temperature for several days, its appearance remained unchanged, and its luminance was virtually invariant.

Comparative Example 1

The procedure of Example 2 was repeated except that a triazole compound having lower molecular weight of the formula:

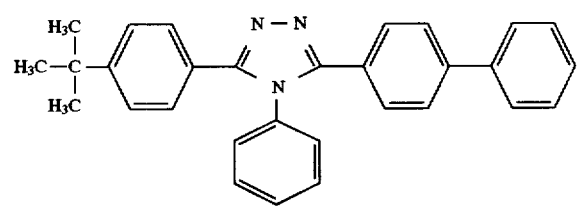

(10)

whose specific resistance was $10^9$ [Ω·cm] was used to form a first electron-transport layer, in place of the oligomerized triazole of this invention. There prepared an organic electroluminescent device. The film thickness of the above triazole compound was 200 Å.

Figure 2B:
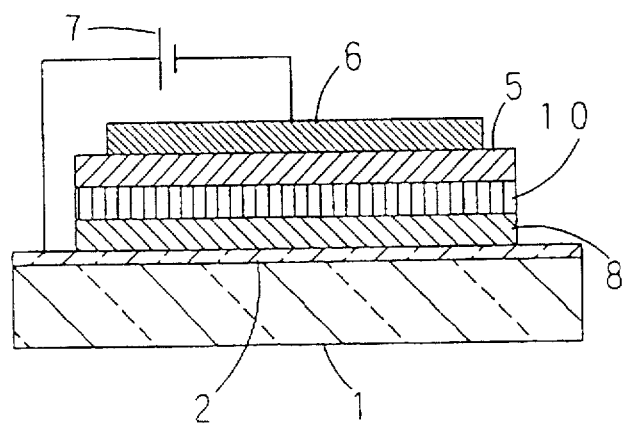
FIG. 2(b) is a sectional view illustrating the layer construction of the organic electroluminescent device prepared in Comparative Example 1 of this invention.

FIG. 2(b) shows the film structure of the organic electroluminescent device thus obtained. In FIG. 2(b), the reference numerals 1, 2 and 5–8 have the same meanings as in FIG. 1(b), and 10 denotes the layer of the triazole derivative having lower molecular weight (the first electron-transport layer).

The luminance of this device was determined in the same manner as described above. At a drive voltage of 14 V, there observed a blue light emission having a luminance of 700 cd/m² originated from the PVK layer 8. When the device was preserved at room temperature for several days, black points occurred on its luminescent surface. And after one-month preservation, its luminance reduced to one-half its initial value.

What we claim is:

1. A triazole derivative of the general formula:

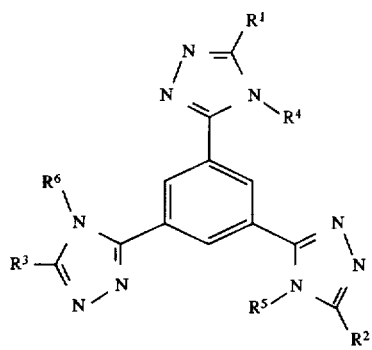
(1)

wherein $R^1$, $R^2$, $R^3$, $R^4$, $R^5$ and $R^6$ may be the same or different, each is hydrogen atom, halogen atom, alkyl, alkoxy, or aryl which may bear a substituent.

2. An organic electroluminescent device having a layer which contains at least one triazole derivative, of the general formula:

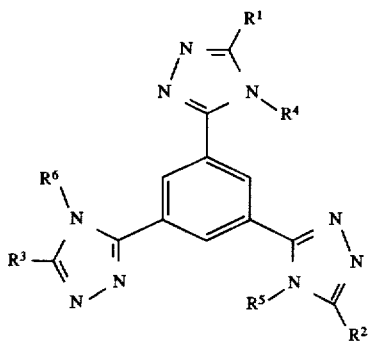
(1)

wherein $R^1$, $R^2$, $R^3$, $R^4$, $R^5$ and $R^6$ may be the same or different, each is hydrogen atom, halogen atom, alkyl, alkoxy, or alyl which may bear a substituent;

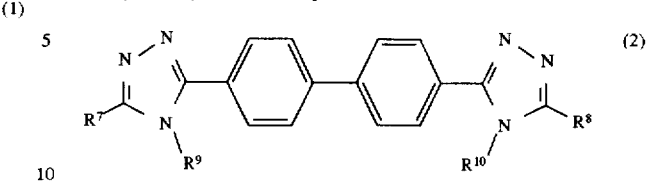
(2)

wherein $R^7$, $R^8$, $R^9$ and $R^{10}$ may be the same or different, each is hydrogen atom, halogen atom, alkyl, alkoxy, or alyl which may bear a substituent.

3. The organic electroluminescent device according to claim 2, wherein said layer is an electron-transport layer containing said triazole derivative as an electron-transport material.

4. The triazole derivative according to claim 1 wherein the alkyl and alkoxy have 1 to 4 carbon atoms and the aryl is a member selected from the group consisting phenyl, tolyl, xylyl, biphenyl, naphthyl, anthryl and phenanthryl.

5. The triazole derivative according to claim 1 wherein said substitutent is a member selected from the group consisting of halogen, cyano and arylamino.

6. The triazole derivative according to claim 1 wherein $R^1$, $R^2$ and $R^3$ are the same and $R^4$, $R^5$ and $R^6$ are the same.

7. The triazole derivative according to claim 1 which is:

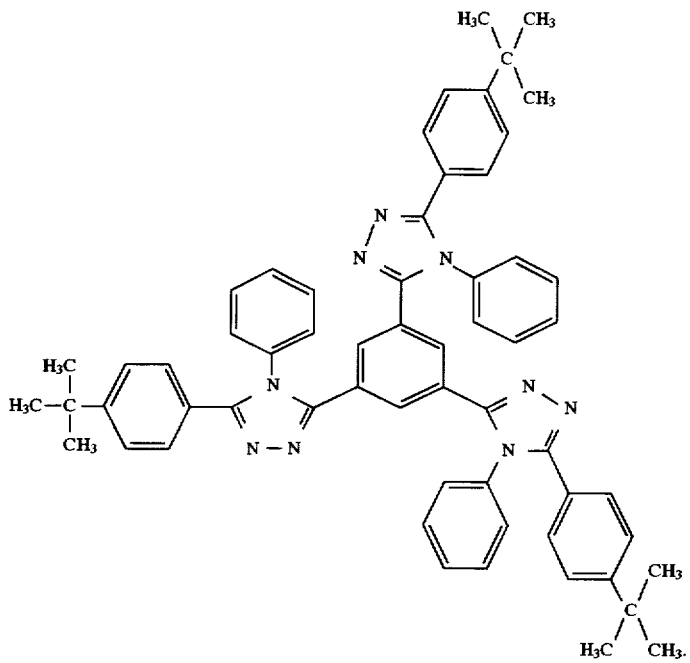

* * * * *

UNITED STATES PATENT AND TRADEMARK OFFICE
CERTIFICATE OF CORRECTION

PATENT NO. : 5,792,567
DATED : August 11, 1998
INVENTOR(S) : Junji Kido, Takashi Uemura, Hiroya Kimura, Nobuyuki Okuda, Yoshinobu Ueba, Yasuko Okuda and Hajime Osaka It is certified that error appears in the above-indentified patent and that said Letters Patent is hereby corrected as shown below:

Title page, item [86] should read --
PCT No. PCT/JP95/00440

§371 Date: Feb. 7, 1996
§102(e) Date: Feb. 7, 1996

Signed and Sealed this

Twelfth Day of January, 1999

Attest:

*Attesting Officer*  *Acting Commissioner of Patents and Trademarks*